United States Patent [19]

Schröder et al.

[11] 4,261,731
[45] Apr. 14, 1981

[54] ALPHA-ISOCYANO-CARBOXYLIC ACID AMIDE COMPOUNDS AND PLANT GROWTH REGULANT COMPOSITIONS

[75] Inventors: Rolf Schröder, Wuppertal; Klaus Lürssen, Bergisch-Gladbach, both of Fed. Rep. of Germany

[73] Assignee: Bayer Aktiengesellschaft, Leverkusen, Fed. Rep. of Germany

[21] Appl. No.: 74,594

[22] Filed: Sep. 11, 1979

[30] Foreign Application Priority Data

Sep. 29, 1978 [DE] Fed. Rep. of Germany ....... 2842639

[51] Int. Cl.³ .................... A01N 53/00; C07C 119/02
[52] U.S. Cl. ...................................... 71/105; 260/464; 260/465.4; 260/465 D
[58] Field of Search ................ 260/464, 465.4, 465 D; 71/105

[56] References Cited

U.S. PATENT DOCUMENTS 4,098,600  7/1978  Chupp .................................. 71/105

FOREIGN PATENT DOCUMENTS 2014  11/1978  European Pat. Off. .
2218009  10/1972  Fed. Rep. of Germany .
2405819  8/1975  Fed. Rep. of Germany .

OTHER PUBLICATIONS

Hoppe et al., Chem. Ber., vol. 109, pp. 482–487 (1976).

Primary Examiner—Dolph H. Torrence
Attorney, Agent, or Firm—Sprung, Felfe, Horn, Lynch & Kramer

[57] ABSTRACT

Alpha-isocyano-carboxylic acid amides of the formula

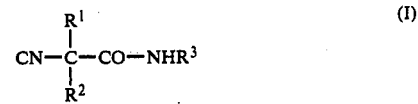

wherein
$R^1$ and $R^2$ are identical or different and each represent hydrogen, alkyl, alkenyl, alkynyl or aralkyl; or
$R^1$ and $R^2$ together represent alkylene; and
$R^3$ is hydrogen, alkyl, alkenyl, alkynyl or aralkyl, with the proviso that at least one of $R^1$, $R^2$ and $R^3$ represents alkyl, alkenyl, alkynyl or aralkyl, or that, in the case where $R^1$ and $R^2$ represent alkylene, $R^3$ represents alkyl, alkenyl, alkynyl or aralkyl, are outstandingly effective for regulating the growth of plants.

19 Claims, No Drawings

ALPHA-ISOCYANO-CARBOXYLIC ACID AMIDE COMPOUNDS AND PLANT GROWTH REGULANT COMPOSITIONS

This invention relates to novel alpha-isocyano-carboxylic acid amide compounds, to plant growth regulant compositions containing them and to methods for regulating plant growth utilizing such compounds.

It is known that (2-chloroethyl)-trimethylammonium chloride has plant growth-regulating properties (see U.S. Pat. No. 3,156,554). However, the activity of this substance is not always completely satisfactory, especially when low amounts are used.

It is also known that 2-chloroethyl-phosphonic acid can be used as a plant growth regulator (see DE-OS (German Published Specification) No. 2,050,245). However, its action also leaves something to be desired when low amounts are used.

The present invention now provides, as new compounds, the alpha-isocyano-carboxylic acid amides of the formula $$CN-\underset{R^2}{\underset{|}{\overset{R^1}{\overset{|}{C}}}}-CO-NHR^3 \qquad (I)$$

wherein
$R^1$ and $R^2$ are identical or different and each represent hydrogen, alkyl, alkenyl, alkynyl or aralkyl; or
$R^1$ and $R^2$ together represent alkylene; and
$R^3$ is hydrogen, alkyl, alkenyl alkynyl or aralkyl, with the proviso that at least one of $R^1$, $R^2$ and $R^3$ represents alkyl, alkenyl, alkynyl or aralkyl, or that, in the case where $R^1$ and $R^2$ represent alkylene, $R^3$ represents alkyl, alkenyl, alkynyl or aralkyl.

It has been found that the alpha-isocyano-carboxylic acid amides of the formula (I) are distinguished by powerful plant growth-regulating properties.

Preferably, in formula (I),
$R^1$ represents hydrogen or straight-chain or branched alkyl with 1 to 5 (especially with 1 to 3) carbon atoms and
$R^2$ represents hydrogen, straight-chain or branched alkyl with 1 to 5 (especially with 1 to 3) carbon atoms, allyl or benzyl, or
$R^1$ and $R^2$ together represent alkylene with 2 to 5 carbon atoms (in particular with 2 carbon atoms), and
$R^3$ represents hydrogen, straight-chain or branched alkyl with 1 to 20 (especially with 1 to 18) carbon atoms, allyl or benzyl, with the proviso that at least one of $R^1$, $R^2$ and $R^3$ represents alkyl, alkenyl, alkynyl or aralkyl.

The invention also provides a process for the preparation of an α-isocyano-carboxylic acid amide of the formula (I), in which an α-isocyano-carboxylic acid ester of the general formula $$CN-\underset{R^2}{\underset{|}{\overset{R^1}{\overset{|}{C}}}}-CO-OR^4 \qquad (II),$$

in which
$R^1$ and $R^2$ have the meanings stated above and
$R^4$ represents lower alkyl, is reacted with an amine of the general formula $$R^3-NH_2 \qquad (III),$$

in which
$R^3$ has the meaning stated above,
if appropriate using a diluent.

Surprisingly, the α-isocyano-carboxylic acid amides according to the invention exhibit a considerably higher plant growth-regulating activity than (2-chloroethyl)-trimethylammonium chloride and 2-chloroethyl-phosphonic acid, which are substances known from the state of the art and are active compounds of high activity and the same type of action.

Specific examples of the α-isocyano-carboxylic acid amides of the formula (I) are given in the following table.

$$CN-\underset{R^2}{\underset{|}{\overset{R^1}{\overset{|}{C}}}}-CO-NH-R^3 \qquad (I)$$

| $R^1$ | $R^2$ | $R^3$ |
|---|---|---|
| CH$_3$ | CH$_3$ | C$_2$H$_5$ |
| CH$_3$ | C$_2$H$_5$ | C$_2$H$_5$ |
| C$_2$H$_5$ | C$_2$H$_5$ | C$_2$H$_5$ |
| H | H | sec.-C$_4$H$_9$ |
| H | H | iso-C$_4$H$_9$ |
| H | H | tert.-C$_4$H$_9$ |
| CH$_3$ | H | n-C$_5$H$_{11}$ |
| CH$_3$ | H | n-C$_6$H$_{13}$ |
| CH$_3$ | H | n-C$_7$H$_{15}$ |
| CH$_3$ | H | n-C$_9$H$_{19}$ |
| —CH$_2$—CH$_2$— | | n-C$_4$H$_9$ |
| —CH$_2$—CH$_2$— | | i-C$_3$H$_7$ |
| —CH$_2$—CH$_2$— | | n-C$_3$H$_7$ |
| —CH$_2$—CH$_2$— | | sec.-C$_4$H$_9$ |
| —CH$_2$—CH$_2$— | | n-C$_5$H$_{11}$ |
| —CH$_2$—CH$_2$— | | n-C$_6$H$_{13}$ |
| —CH$_2$—CH$_2$— | | n-C$_7$H$_{15}$ |
| C$_2$H$_5$ | H | CH$_2$—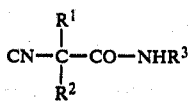 |
| C$_2$H$_5$ | H | CH$_2$—CH=CH$_2$ |
| CH$_3$ | H | CH$_2$—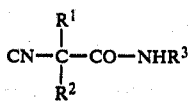 |
| CH$_3$ | CH$_3$ | CH$_2$—CH=CH$_2$ |
| CH$_3$ | CH$_3$ | n-C$_5$H$_{11}$ |
| CH$_3$ | CH$_3$ | n-C$_6$H$_{13}$ |
| CH$_3$ | CH$_3$ | n-C$_7$H$_{15}$ |
| CH$_3$ | CH$_3$ | n-C$_9$H$_{19}$ |
| H | n-C$_5$H$_{11}$ | CH$_3$ |
| H | n-C$_6$H$_{13}$ | CH$_3$ |
| H | n-C$_7$H$_{15}$ | CH$_3$ |
| H | n-C$_9$H$_{19}$ | CH$_3$ |
| H | n-C$_4$H$_9$ | CH$_3$ |

If, for example, α-isocyano-propionic acid methyl ester and ethylamine are used as starting substances, the course of the reaction in the process according to the invention can be represented by the following equation:

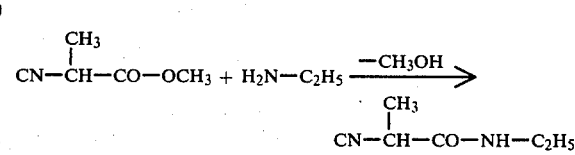

The formula (II) provides a general definition of the α-isocyano-carboxylic acid esters required as starting substances in carrying out the process according to the invention. In this formula, $R^1$ and $R^2$ preferably have those meanings which have already been mentioned as preferred for these radicals in connection with the description of the compounds of the formula (I). $R^4$ preferably represents straight-chain or branched alkyl with 1 to 4 carbon atoms, especially methyl or ethyl.

Examples which may be mentioned of the α-isocyano-carboxylic acid esters of the formula (II) are: α-isocyano-acetic acid methyl ester and ethyl ester, α-isocyano-propionic acid methyl ester and ethyl ester, α-isocyano-butyric acid methyl ester and ethyl ester, α-isocyano-isobutyric acid methyl ester and ethyl ester, α-isocyano-valeric acid methyl ester and ethyl ester, α-isocyano-isovaleric acid methyl ester and ethyl ester, α-isocyano-sec.-valeric acid methyl ester and ethyl ester, α-isocyano-sec.-caproic acid methyl ester and ethyl ester, αisocyano-α-allyl-acetic acid methyl ester and ethyl ester, α-isocyano-α-allyl-propionic acid methyl ester and ethyl ester, α-isocyano-α-benzyl-acetic acid methyl ester and ethyl ester, α-isocyano-α-benzyl-propionic acid methyl ester and ethyl ester and α-isocyano-cyclopropane-carboxylic acid methyl ester and ethyl ester.

The α-isocyano-carboxylic acid esters of the formula (II) are known, or they can be prepared by known processes (see Chem. Ber. 108 (1975), 1580–1592; Angew, Chem. 83 (1971), 357–358 and DE-OS (German Published Specification) No. 2,063,502).

The formula (III) provides a general definition of the amines also to be used as starting substances in the process according to the invention. In this formula, $R^3$ preferably has those meanings which have already been mentioned as preferred for $R^3$ in connection with the description of the substances of the formula (I).

Specific examples which may be mentioned of compounds of the formula (III) are: ammonia, methylamine, ethylamine, propylamine, iso-propylamine, butylamine, iso-butylamine, pentylamine, hexylamine, octylamine, decylamine, dodecylamine, tetradecylamine, hexadecylamine, octadecylamine, allylamine and benzylamine.

The compounds of the formula (III) are known.

The process for the preparation of the α-isocyano-carboxylic acid amides according to the invention is preferably carried out using a suitable solvent or diluent. Possible solvents and diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propionitrile; and alcohols, such as methanol, ethanol and isopropanol.

The reaction temperatures can be varied within a substantial range in carrying out the process according to the invention. In general, the reaction is carried out at temperatures of from 0° C. to 100° C., preferably from 10° C. to 80° C.

In general, the process according to the invention is carried out under normal pressure.

The starting substances are in general employed in equimolar amounts for carrying out the process according to the invention. An excess of one or other of the reactants brings no significant advantages. The reaction is in general carried out in a suitable diluent, and the reaction mixture is stirred at the required temperature for several hours. The reaction mixture is then cooled to 0° to 20° C. and the product which has precipitated out is filtered off. The melting point is used for its characterization. If the product is not obtained as crystals, it is isolated by distilling off the solvent. The refractive index is then used for its characterization.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants as harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time in which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

Some of the α-isocyano-carboxylic acid amides according to the invention not only have plant growth-regulating properties but also exhibit fungicidal activity.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions, for use on seed, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomizing, scattering, dusting, foaming and gassing. Furthermore it is possible to apply the active compounds in accordance with the ultra-low volume method, to spread the active compound preparation or the active compound itself on plants or parts of plants or to inject the active compound preparation or the active compound itself into the soil. It is also possible to treat the seeds of plants.

The active compound concentrates can be varied within a substantial range. In general, 0.01 to 50 kg, preferably 0.05 to 10 kg, of the active compound are employed per hectare of soil surface.

The present invention also provides plant-growth regulating compositions containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The plant-growth regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

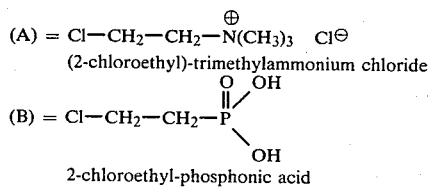

(A) = Cl—CH$_2$—CH$_2$—$\overset{\oplus}{\text{N}}$(CH$_3$)$_3$ Cl$^{\ominus}$
(2-chloroethyl)-trimethylammonium chloride (B) = Cl—CH$_2$—CH$_2$—P$\overset{\text{O}}{\underset{\text{OH}}{\diagup\diagdown}}$OH 2-chloroethyl-phosphonic acid

EXAMPLE A

Influence on growth of woody plants (*Alnus glutinosa*)

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

One-year-old seedlings which had grown to a height of about 25 cm were sprayed with the preparation of active compound until dripping wet. After 6 weeks' growth in a greenhouse, the additional growth was measured and the influence on growth was calculated in % of the additional growth of the control plants. 0% denoted a growth which corresponded to that of the control plants. Positive values characterized a promotion in growth in comparison to the control plants whereas negative values correspondingly indicated an inhibition of growth.

It was found that the active compound (6) had a growth-promoting action in this test, whereas the active compounds (9) and (11) exerted a powerful growth-inhibiting effect.

EXAMPLE B

Stimulation of ethylene biosynthesis or splitting off of ethylene

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Pieces of leaf of identical size were punched from soya bean leaves. These were introduced into vessels which could be closed air-tight, together with 1 ml of the particular preparation of active compound or control solution. These vessels were closed after one hour. After a further 24 hours the ethylene which had collected in the vessels was determined by customary methods of detection. The evolution of ethylene from the pieces of leaf treated with the preparation of active compound was compared with the evolution of ethylene from the controls.

This test was particularly suitable for illustrating the growth-regulating properties of the compounds according to the invention.

The plant hormone ethylene affects numerous processes during the development of the plants. An increase in the amount of ethylene, such as can be achieved with the substances according to the invention, makes it possible to control these processes. The following may be mentioned here as examples of possible actions in which there is a particular commercial interest: detachment of fruit, acceleration of ripening of fruit and leaves, induction of flowering, germination of seeds, thinning-out of fruit, stimulation of latex flux, for example in Hevea, influencing of gender and inhibiting of growth, for example also to prevent the lodging of cereals.

Evaluation of the test results showed that compounds (3), (16), (17), (19), (24), (27) and (32) caused slight stimulation of ethylene biosynthesis, compounds (15), (20), (22), (26) and (31) caused moderate stimulation of ethylene biosynthesis and compounds (14), (25) and (28) caused marked stimulation of ethylene biosynthesis, whereas the known comparison substance (A) caused no stimulation of ethylene biosynthesis.

EXAMPLE C

Inhibition of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth was measured on all the plants and the inhibition of growth in % of the additional growth of the control plants was calculated. 100% meant that growth had stopped and 0% denoted a growth corresponding to that of the control plants.

It was found that compounds (8), (15) and (16) exerted a very powerful growth-inhibiting effect.

EXAMPLE D

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in % of the additional growth of the control plants was calculated. 100% meant that growth had stopped and 0% denoted a growth corresponding to that of the control plants.

It was found that compounds (7), (8), (9) and (11) had a considerably more powerful growth-inhibiting activity than the known comparison substance (B).

EXAMPLE E

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Barley plants were growth to the 2-leaf stage in a greenhouse. In this stage, the plants were sprayed with the preparations of active compound until dripping wet. After 3 weeks, the additional growth was measured on all plants and the inhibition of growth in % of the additional growth of the control plants was calculated. 100% meant that growth had stopped and 0% denoted a growth corresponding to that of the control plants.

It is found that compounds (29) and (30) exerted a powerful growth-inhibiting effect, whereas the known comparison substance (B) had no growth-inhibiting action.

PREPARATIVE EXAMPLES

EXAMPLE 1

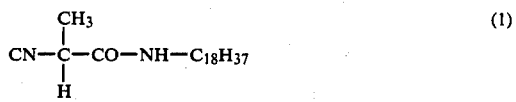

(1)

A solution of 7 g (50 mmols) of α-isocyanopropionic acid ethyl ester and 13.5 g (50 mmols) of octadecylamine in 100 ml of methanol was stirred at 50° C. for 4 hours. Thereafter, it was cooled and the solid which had precipitated was filtered off and rinsed with a few milliliters of methanol. 14.5 g (83% of theory) of α-isocyanopropionic acid octadecylamide with the melting point 59° C. remained.

The following compounds of the formula

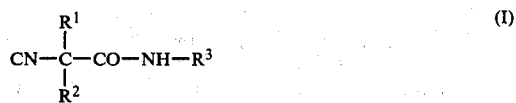

(I)

were prepared analogously to Example 1:

| Example No. | $R^1$ | $R^2$ | $R^3$ | Yield (% of theory) | Physical data (Refractive index; melting point °C.) |
|---|---|---|---|---|---|
| 2 | H | H | $C_4H_9$-n | 80 | 53–54 |
| 3 | $CH_3$ | H | $C_4H_9$-n | 81 | 37 |
| 4 | $CH_3$ | H | $C_3H_7$-iso | 60 | 71 |
| 5 | $CH_3$ | H | $CH_3$ | 81 | 48–49 |
| 6 | H | H | $CH_3$ | 75 | 80 |
| 7 | H | H | $C_3H_7$-iso | 71 | 74 |
| 8 | $CH_3$ | H | H | 70 | 110 |
| 9 | $CH_3$ | H | 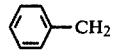 | 50 | 55–65 |
| 10 | $CH_3$ | H | $CH_2=CH-CH_2$ | 90 | $n_D^{20}$:1.4785 |
| 11 | $CH_3$ | H | $C_4H_9$-iso | 85 | 67 |
| 12 | $CH_3$ | $CH_3$ | $CH_3$ | 50 | 60 |
| 13 | $CH_3$ | $CH_3$ | H | 72 | 115–120 |
| 14 | H | H | $C_{12}H_{25}$ | 75 | 68 |
| 15 | H | H | $C_{14}H_{29}$ | 61 | 65 |
| 16 | H | H | $C_{18}H_{37}$ | 83 | 74 |
| 17 | $CH_3$ | H | $C_{12}H_{25}$ | 90 | 72 |

-continued

| Example No. | R¹ | R² | R³ | Yield (% of theory) | Physical data (Refractive index; melting point °C.) |
| --- | --- | --- | --- | --- | --- |
| 18 | $CH_3$ | H | $C_{14}H_{29}$ | 88 | |
| 19 | $C_3H_7$-iso | H | $C_{12}H_{25}$ | 99 | 42 |
| 20 | $C_3H_7$-iso | H | $C_{14}H_{29}$ | 94 | 44 |
| 21 | $C_3H_7$-iso | H | $C_{18}H_{37}$ | 87 | 64 |
| 22 | $CH_3$ | $CH_3$ | $C_{12}H_{25}$ | 93 | |
| 23 | $CH_3$ | $CH_3$ | $C_{14}H_{29}$ | 94 | 38 |
| 24 | $CH_3$ | $CH_3$ | $C_{18}H_{37}$ | 97 | 35 |
| 25 | $CH_3$ | $CH_2=CH-CH_2$ | $C_{14}H_{29}$ | 92 | $n_D^{23}$:1.4631 |
| 26 | | $-CH_2-CH_2-$ | $C_{12}H_{25}$ | 86 | 44 |
| 27 | | $-CH_2-CH_2-$ | $C_{14}H_{29}$ | 85 | 46 |
| 28 | | $-CH_2-CH_2-$ | $C_{18}H_{37}$ | 83 | |
| 29 | H | H | $C_{10}H_{21}$ | 87 | 56 |
| 30 | H | H | $C_8H_{17}$ | 92 | 48 |
| 31 | | $-CH_2-CH_2-$ | H | 91 | 148 |
| 32 | | $-CH_2-CH_2-$ | $CH_3$ | 70 | 52 |

It will be understood that the specification and examples are illustrative, but not limitative of the present invention and that other embodiments within the spirit and scope of the invention will suggest themselves to those skilled in the art.

What is claimed is:

1. Alpha-isocyano-carboxylic acid amide compounds of the formula

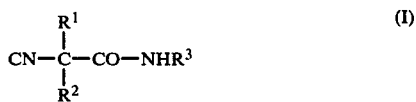

(I)

wherein
R¹ and R² taken together represent alkylene with 2 carbon atoms
R³ is hydrogen, alkyl, alkenyl, alkynyl or aralkyl.

2. Alpha-isocyano carboxylic acid amide compounds as claimed in claim 1 wherein R³ is hydrogen.

3. Alpha-isocyano carboxylic acid amide compounds as claimed in claim 1 wherein R³ is straight-chain or branched alkyl of up to 20 carbon atoms.

4. Alpha-isocyano carboxylic acid amide compounds as claimed in claim 1 wherein R³ is allyl.

5. Alpha-isocyano carboxylic acid amide compounds as claimed in claim 1 wherein R³ is benzyl.

6. Alpha-isocyano carboxylic acid amide compounds as claimed in claim 1 wherein R³ is alkyl with up to 18 carbon atoms.

7. Alpha-isocyano carboxylic acid amide compounds as claimed in claim 1 wherein R³ is alkyl or benzyl.

8. Alpha-isocyano carboxylic acid amide compound as claimed in claim 1 designated alpha-isocyanocyclopropionic acid dodecylamide.

9. Alpha-isocyano carboxylic acid amide compound as claimed in claim 1 designated alpha-isocyanocyclopropionic acid octadecylamide.

10. Alpha-isocyano carboxylic acid amide compound as claimed in claim 1 designated alpha-isocyanocyclopropionic acid amide.

11. Alpha-isocyano carboxylic acid amide compound as claimed in claim 1 designated alpha-isocyanocyclopropionic acid methylamide.

12. Plant growth regulant composition comprising an agriculturally acceptable carrier and, in plant growth regulatingly effective amounts, an alpha-isocyano carboxylic acid amide compound as claimed in claim 1.

13. Method of regulating plant growth which method comprises applying to the plants, or their habitat a plant growth regulatingly effective amount of an alpha-isocyano carboxylic acid amide compound as claimed in claim 1.

14. Method as claimed in claim 13 wherein alpha-isocyano carboxylic acid amide compound is selected from
alpha-isocyanocyclopropionic acid dodecylamide;
alpha-isocyanocyclopropionic acid octadecylamide;
alpha-isocyanocyclopropionic acid amide; and
alpha-isocyanocyclopropionic acid methylamide.

15. Method as claimed in claim 13 wherein said compound is applied at a dosage of 0.1 to 50 kg per hectare.

16. Method as claimed in claim 13 wherein said compound is applied to a dosage of 0.05 to 10 kg per hectare.

17. Method as claimed in claim 13 wherein the growth of plants is stimulated.

18. Method as claimed in claim 13 wherein the growth of plants is inhibited.

19. Method as claimed in claim 13 wherein the growth of plants is altered.

* * * * *